United States Patent [19]

Shutske et al.

[11] Patent Number: 4,579,981
[45] Date of Patent: Apr. 1, 1986

[54] PROCESS FOR THE PREPARATION OF 2-CHLORO-1,3-DIMETHOXYBENZENE

[75] Inventors: Gregory M. Shutske, Nauheim, Fed. Rep. of Germany; Thomas B. K. Lee, Whitehouse Station; Gregory M. Jobin, Bridgewater, both of N.J.

[73] Assignee: Hoechst-Roussel Pharmaceuticals Inc., Somerville, N.J.

[21] Appl. No.: 640,264

[22] Filed: Aug. 13, 1984

Related U.S. Application Data

[63] Continuation of Ser. No. 270,426, Jun. 4, 1981, abandoned.

[51] Int. Cl.$^4$ ............................................. C07C 41/22
[52] U.S. Cl. .................................................... 568/649
[58] Field of Search ........................ 568/649; 570/207

[56] References Cited

PUBLICATIONS

Boltze et al., Ann. Chem., 709, (1967), 63–69.
Tamborski et al., Chem. & Industry (London), (1965), 2067–2068.
Gay et al., Chem. & Industry (London), (1966), 1635.
Meyers et al., J. Org. Chem., vol. 40, No. 21, (1975), 3158–3159.
Gschwend et al., Organic Reactions, vol. 26, (1979), 1–5, 56 & 83.
Gilman et al., Jour. Amer. Chem. Soc., vol. 61, (1939), 1371–1373.
Gilman et al., Jour. Amer. Chem. Soc., vol. 62, (1940), 1843–1846.
Langham et al., Jour. Amer. Chem. Soc., vol. 63, (1941), 545–549.
Weygand/Hilgetag, Preparative Organic Chemistry, (1972), 758–759.

*Primary Examiner*—Bernard Helfin
*Attorney, Agent, or Firm*—Raymond R. Wittekind

[57] ABSTRACT

An improved process for the preparation of 2-chloro-1,3-dimethoxybenzene involving the reaction of [2,6-dimethoxyphenyl]lithium with chlorinating agents is disclosed. 2-Chloro-1,3-dimethoxybenzene is useful as a starting material for the synthesis of pharmacologically valuable 1,2-benzisoxazoloxyacetic acids.

4 Claims, No Drawings

PROCESS FOR THE PREPARATION OF 2-CHLORO-1,3-DIMETHOXYBENZENE

This is a continuation of application Ser. No. 270,426 filed June 4, 1981 and now abandoned.

BACKGROUND OF THE INVENTION

The commercial feasibility of processes for the preparation of pharmacologically valuable compounds depends, for the most part, upon the availability and cost of the starting material or materials thereof. For example, the commercial feasibility of the process described in U.S. patent application Ser. No. 949,128, filed Oct. 6, 1978, now abandoned, for the preparation of certain diuretic, uricosuric and antihypertensive 1,2-benzisoxazoloxyacetic acids and derivatives thereof depends, in part, upon the availability and cost of 2-chloro-1,3-dimethoxybenzene. See Reaction Scheme I. A process for the preparation of 2-chloro-1,3-dimethoxybenzene was disclosed by N. Schamp in Bull. Chem. Soc. Belges, 73, 35 (1964); Chem. Abs., 60, 7945h (1964) and P. Kovacic and M. E. Kurz in J. Org. Chem., 31, 2459 (1966). This process, however, involves three steps from commercially available cyclohexane-1,3-dione, namely, the chlorination of cyclohexane-1,3-dione followed by dehydrochlorination of the resulting 2,2-dichlorocyclohexane-1,3-dione to 2-chloro-1,3-dihydroxybenzene, as described by N. Schamp, and methylation thereof to 2-chloro-1,3-dimethoxybenzene, as described by P. Kovacic and M. E. Kurz, and thus would apparently furnish the desired chloro compound was difficulty and in relatively low yield, even if the individual steps proceed in relatively high yield. See Reaction Scheme II. The economics of a process for the preparation of 2-chloro-1,3-dimethoxybenzene would be substantially improved and the availability of this compound for the preparation of pharmacologically important 1,2-benzisoxazoloxyacetic acids would be materially increased if a shorter, technically simpler and more efficient method than that described in the aforementioned references were available. The present invention involves such a short, technically simple and apparently more efficient and less costly process for the preparation of 2-chloro-1,3-dimethoxy-benzene. See Reaction Scheme III.

DETAILED DESCRIPTION OF THE INVENTION

The present invention relates to a novel, efficient and relatively inexpensive process for the preparation of 2-chloro-1,3-dimethoxybenzene. More particularly, the present invention relates to a short, technically simple process for the preparation of 2-chloro-1,3-dimethoxybenzene involving lithiating 1,3-dimethoxybenzene to [2,6-dimethoxyphenyl]lithium and contacting the lithio derivative with a chlorinating agent.

As used throughout the specification and appended claims, the terms "polychloroalkane" refers to an alkane, i.e., a straight or branched chain saturated hydrocarbon, having the empirical formula $C_nH_{2n+2}$ where n is 1 to 6 such as methane, ethane, propane, butane, 2-methylbutane, 3-methylpentane and the like, in which the hydrogen atoms have been replaced by chlorine atoms, such as tetrachloromethane, hexachloroethane, octachloropropane, decachlorobutane,1,1,1,2,3,3,4,4,4-nonachloro-2-trichloromethylbutane,1,1,1,2,24,5,5,6,6-undecachloro-3-trichloromethylpentane and the like.

The term "polychloroalkanone" refers to a polychloroalkane having 3 to 6 carbon atoms in which a dichloromethylene moiety is replaced by a carbonyl function such as hexachloropropane-2-one, octachlorobutan-2-one-1,1,1,3,4,4,4-heptachloro-3-trichloromethylbutan-2-one,1,1,1,3,4,4,5,5,5-nonachloro-3-trichloromethylpentan-2-one and the like.

The process of the present invention for the preparation of 2-chloro-1,3-dimethoxybenzene is illustrated in Reaction Scheme III.

In this process, readily available 1,3-dimethoxybenzene 1 is converted to the 2-lithio derivative, [2,6-dimethoxyphenyl]lithium 2 by conventional methods well known in the art. Typically, 1,3-dimethoxybenzene dissolved in a suitable solvent, such as diethyl ether or 1,2-dimethoxyethane, is treated with a slight excess of n-butyllithium and the reaction mixture is either allowed to stand at ambient temperature for, for example, about one to 16 hours, or heated under reflux for about the same time period to complete the conversion. See, for example, K-H. Boltze, et al., Ann. Chem., 709, 63 (1967). Generally without isolation, the lithio derivation 2 is transformed to 2-chloro-1,3-dimethoxybenzene by treatment with a chlorinating agent. Among chlorinating agents, there may be mentioned chlorine, N-chloroimides such as N-chlorosuccinimide, N-chlorophthalimide and the like and polychloroalkanes having 1 to 6 carbon atoms and polychloroalkanes having 3 to 6 carbon atoms, such as those hereinbefore defined. Of the N-chloroimides, N-chlorosuccinimide is preferred. Of the polychloroalkanes, tetachloromethane and hexachloroethane are preferred. Of the polychloroalkanones, hexachloropropan-2-one is preferred. Hexachloroethane is most preferred.

The transformation of the lithio derivative 2 to the desired chlorobenzene 3 is suitably performed in an inert solvent. Suitable inert solvents include ethereal solvents, such as, for example diethyl ether, tetrahydrofuran, dioxane, 1,2-dimethoxyethane, dimethoxyethoxyethane and the like. The preferred solvent is diethyl ether.

The relative molar amounts of lithio derivative 2, as defined by the initial molar amount of 1,3-dimethoxybenzene 3, and chlorinating agents are not narrowly critical and excess chlorinating agent may be employed. Generally, small molar excess of the chlorinating agent in the order of about 5 to 10% is preferred to promote the conversion of 2 to 3 without causing purification problems. When chlorine is employed as the chlorinating agent, however, it is desirable to limit the molar excess of chlorine to about 10% to avoid possible complicating side-reactions.

While the reaction temperature is also not narrowly critical, it is preferred to perform the conversion of 2 to 3 at a temperature at which the reaction proceeds to completion at a convenient rate. When N-chloroimides are employed as the chlorinating agent, the reaction proceeds at a convenient rate at a temperature within the range of about 35° C. to 75° C., a most convenient rate being attained at a temperature of about 55° C. When polychloroalkanes are utilized, the reaction proceeds at a convenient rate at a temperature within the range of about −80° C. to about 35° C., a most convenient rate being attained at a reaction temperature of about 25° C. When polychloroalkanones are chosen as the chlorinating agent, the conversion proceeds at a convenient rate at a temperature within the range of about −75° C. to about 25° C., a most convenient rate being attained at a temperature of about 0° C. In the case of chlorine, i.e., when gaseous chlorine is used as the chlorinating agent, a convenient raction rate is attained at a temperature within the range of about 30° C. to 50° C., a most convenient rate being attained at a temperature at about 50° C.

2-Chloro-1,3-dimethoxybenzene is useful as a starting material for the preparation of 7-chloro-1,2-benzisoxazoloxyacetic acids and derivatives thereof, which show diuretic, uricosuric and antihypertensive properties. See U.S. patent application Ser. No. 949,128, filed Oct. 6, 1978, now abandoned.

The following example is for illustrative purposes only and is not to be construed as limiting the invention described herein in any way whatsoever.

EXAMPLE

Preparation of 2-Chloro-1,3-dimethoxybenzene (a) N-Chlorosuccimide Method

To a solution of 1,3-dimethoxybenzene (13.8 g) in 1,2-dimethoxyethane (100 ml) is added 2.6M n-butyllithium (40 ml). After 40 minutes, N-chlorosuccinimide (13.5 g) is added and the reaction temperature is maintained below 55° C. by means of an ice-bath. After an additional 45 minutes, the reaction mixture is poured into water and extracted with ether. Evaporation of the organic extract affords an oil which is choromatographed on silica gel (125 g), eluting with 20% ether-hexane. Evaporation of the eluents affords an oil which crystallized on standing. Recrystallization from hexane gives 2-chloro-1,3-dimethoxybenzene, mp 62°-64° C.

ANALYSIS: Calculated for $C_8H_9ClO_2$: 55.66%C, 5.25%H, 20.54%Cl. Found: 55.75%C, 5.20%H, 20.24%Cl.

(b) Chlorine Method

Gaseous chlorine is condensed in a receptacle immersed in a dry ice-acetone bath until 2.5 ml is collected. The bath is removed and the chlorine is allowed to evaporate into a solution of [2,6-dimethoxyphenyl]lithium in 1,2-dimethoxyethane, prepared by adding 2.6M n-butyllithium (10 ml) to 1,3-dimethoxybenzene (6.9 g) dissolved in dimethoxyethane (50 ml) maintained at less than 50° C. by means of an ice-bath and permitting the resulting solution to stand for 40 minutes. After one hour, the reaction mixture is poured into water and extracted with ether. The ethereal extracts are dried, filtered and evaporated to afford an oil. A comparison of the proton magnetic resonance spectrum of the oil with that of authentic 2-chloro-1,3-dimethoxybenzene prepared by Method (a) indicated that the reaction product contained 62% of the 2-chloro compound.

(c) Hexachloroethane Method

To a solution of 1,3-dimethoxybenzene (13.8 g) in dry ether (50 ml, freshly distilled from sodium benzophenone ketyl) is added dropwise 2.4M n-butyllithium (50 ml) at 5° C. over five minutes. After the addition is complete, the mixture is heated under reflux for two and one-half hours and then cooled to −2° C. To the cooled mixture is added dropwise a solution of hexachloroethane (30.9 g) in dry ether (80 ml) over 23 minutes, during which time the reaction temperature increased to 14° C. After this addition is complete, the reaction mixture is allowed to warm to room temperature and is stirred at room temperature overnight. The reaction mixture is cooled to 5° C. and water (50 ml) is added. The layers are separated and the ether layer is washed with water (50 ml). The aqueous phase is extracted with ether (50 ml) and the combined organic extracts are dried over anhydrous magnesium sulfate, filtered and evaporated. Recrystallization of the residue from hexane (60 ml) yields 2-chloro-1,3-dimethoxybenzene (12.3 g, 71.5%), mp 71°-73° C. (reported mp 69°-71° C., P. Kovacic and M. E. Kurtz, ibid. page 2465).

Variations of the basic process involving reaction times, reaction temperatures and reaction solvents did not materially alter the overall results of the method.

(d) Carbon Tetrachloride Method

To a solution of 1,3-dimethoxybenzene (13.8 g) in dry ether (50 ml, freshly distilled over sodium benzophenone ketyl) is added dropwise 2.2M n-butyllithium over a period of 15 minutes, maintaining the reaction temperature at 31° C. After the addition is complete, the reaction mixture is heated under reflux for two hours and stirred at room temperature overnight. The reaction mixture is cooled to −75° to −78° C. and a solution of carbon tetrachloride (10.6 ml) in dry ether (20 ml) is added dropwise over a period of 1 hour and 15 minutes, maintaining the reaction temperature at less than −65° C. After the addition is complete, the reaction mixture is stirred at about −70° C. for one hour and allowed to warm to room temperature over a two-hour period. The reaction mixture is cooled to 0° C. and ice water (50 ml) and 3N hydrochloric acid (75 ml) are added. Toluene (150 ml) is added. The mixture is filtered and the layers are separated. The aqueous layer is extracted with toluene (60 ml) and the combined organic fractions are washed with 5% sodium chloride solution (100 ml), dried over anhydrous potassium carbonate, filtered and concentrated to afford an oil (20 g). Gas chromatographic analysis of the oil indicated that it contained predominantly 2-chloro-1,3-dimethoxybenzene together with minimum amounts of starting material, 1,3-dimethoxybenzene.

Ether (60 ml) and hexane (20 ml) are added to the oil. The resulting solid is collected. Gas chromatographic analysis of the solid indicates that it also contains predominantly 2-chloro-1,3-dimethoxybenzene together with lesser amounts of the starting 1,3-dimethoxybenzene.

(e) Hexachloroacetone Method

To a solution of 1,3-dimethoxybenzene (13.8 g) in dry ether (50 ml, freshly distilled from sodium benzophenone ketyl) is added dropwise 2.4M n-butyllithium (50 ml) at 5° C. over five minutes. After the addition is complete, the mixture is heated under reflux for two and one-half hours and then cooled to −65° C. To the cooled mixture is added dropwise a solution of hexachloroacetone (19.8 ml) in dry ether (50 ml) over one hour. The reaction mixture is allowed to warm to 0° C. and after one hour, water (50 ml) is added and the combined aqueous phases are extracted with ether. The combined ether fractions are dried over anhydrous magnesium sulfate and filtered. The filtrate is washed with 15% sodium sulfate solution, dried over anhydrous magnesium sulfate, filtered and evaporated. Trituration of the residue with hexane (41 ml) affords 2-chloro-1,3-dimethoxybenzene (8.6 g, 50%) as a gum.

The gas-liquid chromatogram of the gum showed that it contained predominantly the desired 2-chloro compound.

REACTION SCHEME I

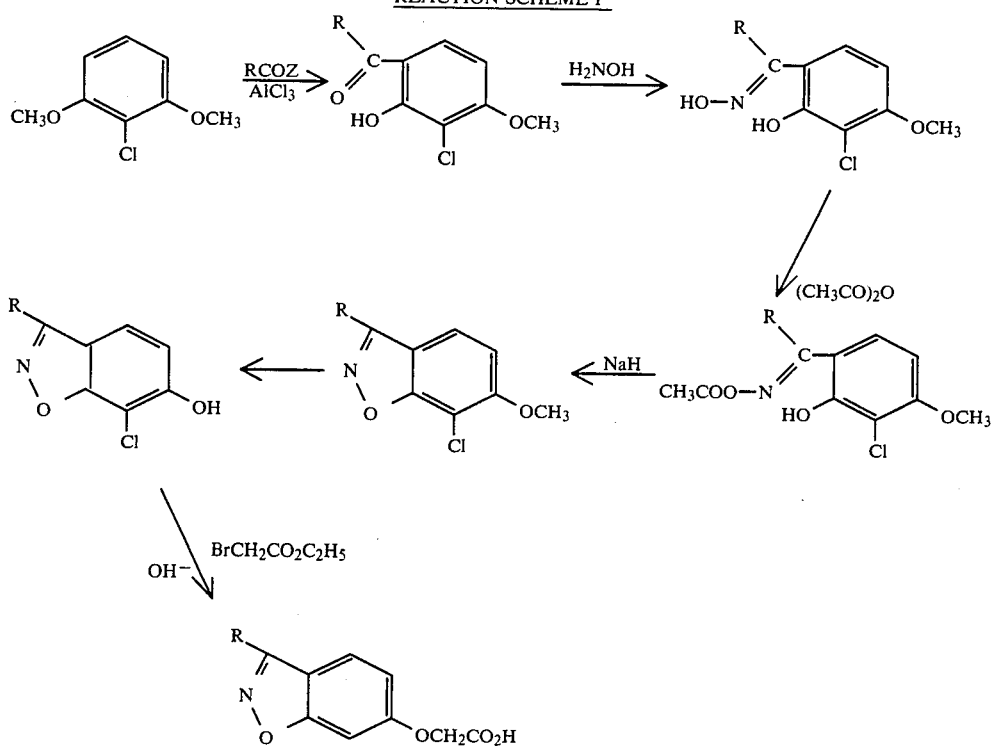

wherein R and Z are as described in U.S. Pat. Application Ser. No. 949,128, filed October 6, 1978, now abandonded.

REACTION SCHEME II

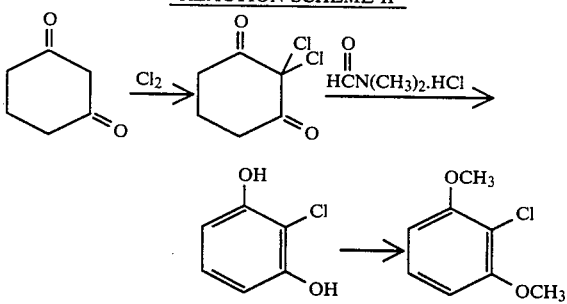

REACTION SCHEME III

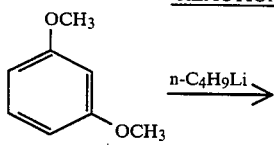

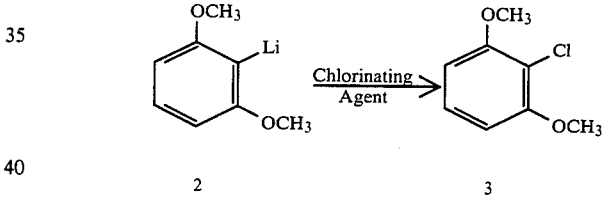

We claim:

1. A process for the preparation of 2-chloro-1,3-dimethoxybenzene which comprises contacting [2,6-dimethoxyphenyl]lithium with a chlorinating agent selected from the group consisting of polychloroalkanes of 1 to 6 carbon atoms and polychloroalkanones of 3 to 6 carbon atoms, all of the hydrogen atoms of which have been replaced by chlorine atoms, in the presence of diethyl ether solvent, which solvent had been pretreated with sodium benzophenone ketyl.

2. The process of claim 1 wherein the polychloroalkane is carbon tetrachloride.

3. The process of claim 1 wherein the polychloroalkane is hexachloroethane.

4. The process of claim 1 wherein the polychloroalkanone is hexachloroacetone.

* * * * *